US011298332B2

(12) United States Patent
Hanlon et al.

(10) Patent No.: US 11,298,332 B2
(45) Date of Patent: Apr. 12, 2022

(54) COMPOSITIONS FOR THERAPY AND HEALTH CONTAINING AMINO ACIDS WITH BITTER TASTE

(71) Applicant: AXCELLA HEALTH INC., Cambridge, MA (US)

(72) Inventors: Thomas Hanlon, Concord, MA (US); Andrew M. Wood, Newtown, PA (US)

(73) Assignee: AXCELLA HEALTH INC., Cambridge, MA (US)

(*) Notice: Subject to any disclaimer, the term of this patent is extended or adjusted under 35 U.S.C. 154(b) by 0 days.

(21) Appl. No.: 16/446,192

(22) Filed: Jun. 19, 2019

(65) Prior Publication Data

US 2019/0388375 A1 Dec. 26, 2019

Related U.S. Application Data

(60) Provisional application No. 62/687,715, filed on Jun. 20, 2018.

(51) Int. Cl.
| | |
|---|---|
| *A61K 31/198* | (2006.01) |
| *A23L 27/00* | (2016.01) |
| *A23L 29/269* | (2016.01) |
| *A23L 27/30* | (2016.01) |
| *A23L 29/00* | (2016.01) |
| *A23L 33/175* | (2016.01) |
| *A61K 31/205* | (2006.01) |
| *A61K 31/405* | (2006.01) |
| *A61K 31/4172* | (2006.01) |
| *A61K 47/12* | (2006.01) |
| *A61K 47/22* | (2006.01) |
| *A61K 47/26* | (2006.01) |
| *A61K 47/36* | (2006.01) |

(52) U.S. Cl.
CPC ............ *A61K 31/198* (2013.01); *A23L 27/33* (2016.08); *A23L 27/84* (2016.08); *A23L 27/88* (2016.08); *A23L 29/055* (2016.08); *A23L 29/27* (2016.08); *A23L 33/175* (2016.08); *A61K 31/205* (2013.01); *A61K 31/405* (2013.01); *A61K 31/4172* (2013.01); *A61K 47/12* (2013.01); *A61K 47/22* (2013.01); *A61K 47/26* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 6,090,401 A * | 7/2000 | Gowan, Jr. .......... | A61K 9/0056 424/439 |
| 6,180,155 B1 | 1/2001 | Lotz et al. | |
| 9,878,004 B2 | 1/2018 | Williams et al. | |
| 2002/0187180 A1 | 12/2002 | Calton et al. | |
| 2004/0087490 A1* | 5/2004 | Troup ..................... | A61P 21/06 514/5.5 |
| 2004/0197401 A1 | 10/2004 | Calton et al. | |
| 2004/0213838 A1 | 10/2004 | Mazer et al. | |
| 2006/0073254 A1 | 4/2006 | Catani et al. | |
| 2007/0286909 A1* | 12/2007 | Smith .................. | A61K 31/455 424/682 |
| 2010/0119692 A1 | 5/2010 | Hamman et al. | |
| 2011/0195115 A1* | 8/2011 | Tanaka ................... | A61P 37/04 424/451 |
| 2016/0339078 A1 | 11/2016 | Hamill et al. | |
| 2018/0125926 A1 | 5/2018 | Williams et al. | |

FOREIGN PATENT DOCUMENTS

| | | |
|---|---|---|
| CN | 103393072 A | 11/2013 |
| CN | 105360846 A | 3/2016 |
| EP | 2324826 A1 | 5/2011 |
| JP | 2003235512 A | 8/2003 |
| JP | 2003274896 A | 9/2003 |
| JP | 2012136492 A | 7/2012 |
| JP | 2017123841 A | 7/2017 |
| KR | 100970664 B1 | 7/2010 |
| WO | 2004026294 A1 | 4/2004 |
| WO | 2004058242 A1 | 7/2004 |
| WO | 2005065726 A1 | 7/2005 |
| WO | 2006062238 A1 | 6/2006 |
| WO | 2006102451 A2 | 9/2006 |
| WO | 2014172341 A1 | 10/2014 |
| WO | 2015048333 A2 | 4/2015 |
| WO | 2015048340 A2 | 4/2015 |
| WO | 2015048342 A2 | 4/2015 |
| WO | 2015048345 A2 | 4/2015 |
| WO | 2015048346 A2 | 4/2015 |
| WO | 2015048348 A2 | 4/2015 |
| WO | 2016003263 A1 | 1/2016 |
| WO | 2018173986 A1 | 9/2018 |

OTHER PUBLICATIONS

International Search Report and Written Opinion issued in PCT/US2019/037977, dated Sep. 26, 2019.
Kim et al., "Mechanisms of Aqueous Foam Stability and Antifoaming Action," Journal of Ind & Eng Chemistry (1997) vol. 3, No. 2, pp. 138-146.
Lobo et al., "Foam mat drying of Tommy Atkins mango: Effects of air temperature and concentrations of soy lecithin and carboxymethylcellulose on phenolic composition, mangiferin, and antioxident capacity," Food Chemistry (2017) vol. 221, pp. 258-266.
Louin et al., "Plasma concentrations of arginine and related amino acids following traumatic brain injury: Proline as a promising biomarker of brain damage," Nitric Oxide: Biology and Chemistry (2017) vol. 17, No. 2, pp. 91-97.
Martina et al., "Long-Term N-Acetylcysteine and L-Arginine Administration Reduces Endothelial Activation and Systolic Blood Pressure in Hyptertensive Patients With Type 2 Diabetes," Diabetes Care (2008) vol. 31, No. 5, pp. 940-944.
Tsuda et al., "Combined Effect of Arginine, Valine, and Serine on Excercise-Induced Fatigue in Healthy Volunteers: A Randomized, Double-Blind, Placebo-Controlled Crossover Study," Nutrients (2019) vol. 11, Article 862, 12 pages.

\* cited by examiner

*Primary Examiner* — Nannette Holloman
(74) *Attorney, Agent, or Firm* — Lando & Anastasi, LLP

(57) ABSTRACT

This disclosure provides a dry powder formulation of free amino acids with an acceptable and even good taste profile.

28 Claims, 4 Drawing Sheets

APPENDIX A

Table 17: Experimental Variable Formulas and Reconstitution Protocol

FORMULAS:

| Lot Number | Supplier | Variable Formula Number<br>Ingredient | BLEND 1<br>106084a<br>Amount per Packet (g) | BLEND 2<br>106084b<br>Amount per Packet (g) | BLEND 3<br>106085a<br>Amount per Packet (g) | BLEND 4<br>106086b<br>Amount per Packet (g) | PLACEBO<br>106085b<br>Amount per Packet (g) |
|---|---|---|---|---|---|---|---|
| OH704 01/19 | Ajinomoto | Fusi-BCAA Instantized Blend | 2.00 | 2.00 | 1.33 | 2.00 | |
| | | L-Leucine | | | 0.67 | | |
| | | L-Isoleucine | | | | | |
| | | L-Valine | | | | | |
| RO04T0310036 | Ajinomoto | Arginine HCl | 1.50 | 1.50 | 1.50 | 1.50 | |
| RO14T0150007 | Ajinomoto | Glutamine | 2.00 | 2.00 | 2.00 | 2.00 | |
| 1EF1057 | Spectrum Chems | Acetylcysteine | 0.25 | 0.25 | 0.25 | 0.25 | |
| R831T0020004 | Ajinomoto | Tryptophan | | 1.00 | | | |
| R024P0010003 | Ajinomoto | Lysine Acetate | | | | 0.25 | |
| R830T0020002 | Ajinomoto | Threonine | | | | 0.17 | |
| R816T0030036 | Ajinomoto | Histidine | | | | 0.08 | |
| R827T0020009 | Ajinomoto | Phenylalanine | | | | 0.08 | |
| M1501295 | GPC | Maltrin QD M500 Maltodextrin NF | | | | | 5.75 |
| 1DH0229 | Spectrum Chems | Citric Acid | 0.67 | 0.67 | 0.67 | 0.67 | 0.98 |
| R560003303 | Am Lec Co | Alecolec F100 | 0.83 | 0.83 | 0.83 | 0.83 | 0.59 |
| 29791 | TIC Gums | XanthanTicaxan Rapid-3 | 0.24 | 0.24 | 0.24 | 0.24 | 0.24 |
| 2EF0548 | Spectrum Chems | Ace-K | 0.05 | 0.09 | 0.05 | 0.05 | 0.04 |
| MC15C92311 | Tate & Lyle | Splenda Sucralose Micronized NF | 0.03 | 0.03 | 0.03 | 0.03 | 0.02 |
| M5078 | David Michael | Vanilla Custard #4306 | 0.06 | 0.06 | 0.06 | 0.06 | 0.06 |
| 6R1120 | David Michael | Nat Orange WONF #1326 | 0.36 | 0.36 | 0.36 | 0.36 | 0.36 |
| H214036 | FONA | Lime 865.0032U | 0.05 | 0.05 | 0.05 | 0.05 | 0.05 |
| S1630722 | FONA | Lemon 862.2169U | 0.05 | 0.05 | 0.05 | 0.05 | 0.05 |
| S1624410 | FONA | Bitterness Masking 936.2160U | 0.12 | 0.18 | 0.12 | 0.12 | 0.12 |
| AW6705 | Sensient | FD&C Yellow 6 | 0.01 | 0.01 | 0.01 | 0.01 | 0.01 |
| AW7914 | Sensient | FD&C Red 40 (1:100 in M500) | | | | | 0.07 |
| | | Total | 8.22 | 9.31 | 8.22 | 8.80 | 8.33 |

RECONSTITUTION PROTOCOL:
1. Accurately weigh 4 fluid oz (118.3 g) of distilled water into an 8 oz bottle (Nalgene 2189-0008, HDPE)
2. Tear open 1 stick pack and pour powder into bottle, flick stick pack while inverted to transfer as much powder as possible
3. Seal bottle and shake vigorously for 20-30 seconds
4. Open bottle and dispense 3 - 6 (depending on number of tasters) equal aliquotes to cups for organoleptic evaluation

Figure 1

Table 18:

Intensity scores for each attribute tested (1 to 5 scale, lower number = lower intensity) at time points 0 months and 1 month of storage at refrigerated conditions

| | Time Point (month) | Color | Orange Aroma | Off-Aroma | Orange Flavor | Off-Flavor | Aftertaste | Texture |
|---|---|---|---|---|---|---|---|---|
| Placebo | 0 | 4.3 | 3.3 | 1.5 | 4.3 | 1.5 | 2.0 | 2.5 |
| | 1 | 3.8 | 3.0 | 1.2 | 4.0 | 1.0 | 1.5 | 2.5 |
| Blend 1 | 0 | 3.0 | 3.3 | 1.2 | 3.7 | 2.0 | 2.5 | 2.5 |
| | 1 | 3.0 | 3.3 | 1.2 | 3.3 | 2.0 | 2.0 | 2.3 |
| Blend 2 | 0 | 4.3 | 3.2 | 1.3 | 2.3 | 3.8 | 3.5 | 2.8 |
| | 1 | 4.8 | 3.2 | 1.3 | 2.2 | 3.5 | 4.0 | 2.7 |
| Blend 3 | 0 | 3.5 | 3.2 | 1.5 | 3.5 | 2.5 | 2.3 | 2.7 |
| | 1 | 2.8 | 2.8 | 1.5 | 3.0 | 1.7 | 2.2 | 2.7 |
| Blend 4 | 0 | 3.7 | 2.7 | 1.8 | 3.2 | 3.2 | 3.2 | 2.7 |
| | 1 | 3.0 | 2.4 | 2.7 | 2.8 | 1.8 | 2.0 | 2.8 |

Figure 2

Table 19:
DOD scores for Overall DOD (0 to 7 scale*) at time points 1, 2 and 3 months comparing refrigerated controls to samples held at accelerated conditions

| Month | Placebo | Blend 1 | Blend 2 | Blend 3 | Blend 4 |
|---|---|---|---|---|---|
| 1 | 0.8 | 1.5 | 0.8 | 1.1 | 0.7 |
| 2 | 0.8 | 2.1 | 2.1 | 2.3 | 1.4 |
| 3 | 2.1 | 2.4 | 4.7 | 4.1 | 2.7 |

| * | Scale Key | Difference |
|---|---|---|
| | 0 | none |
| | 1 | very small |
| | 2 | small |
| | 3 | small/moderate |
| | 4 | moderate |
| | 5 | moderate/large |
| | 6 | large |
| | 7 | very large |

Figure 3

Table 20:

DOD scores for Overall DOD (0 to 7 scale*) at time points 1, 3, 4.5, 6 and 12 months comparing refrigerated controls to samples held at ambient conditions

| Month | Placebo | Blend 1 | Blend 2 | Blend 3 | Blend 4 |
|---|---|---|---|---|---|
| 1 | 1.0 | 2.0 | 1.3 | 1.3 | 1.2 |
| 3 | 1.4 | 1.8 | 2.4 | 0.8 | 2.5 |
| 4.5 | 1.2 | 1.0 | 0.8 | 0.8 | 1.2 |
| 6 | 1.7 | 1.5 | 2.7 | 2.2 | 1.7 |
| 12 | 1.8 | 2.6 | 2.0 | 2.2 | 1.0 |

\*

| Scale Key | Difference |
|---|---|
| 0 | none |
| 1 | very small |
| 2 | small |
| 3 | small/moderate |
| 4 | moderate |
| 5 | moderate/large |
| 6 | large |
| 7 | very large |

COMPOSITIONS FOR THERAPY AND HEALTH CONTAINING AMINO ACIDS WITH BITTER TASTE

RELATED APPLICATIONS

This application claims priority to U.S. Ser. No. 62/687,715 filed Jun. 20, 2018, the contents of which is incorporated herein by reference in its entirety.

BACKGROUND

Mixtures of solids, e.g., amino acids, have many uses in the food and pharmaceutical industries.

Now it has been discovered that mixtures of amino acids and related molecules can treat various disease states by rebalancing patients' metabolic state to address serious unmet medical needs. These endogenous metabolic modulators treat the multifactorial etiology of serious diseases by reprogramming disordered metabolism in an unprecedented, coordinated, multifactorial manner.

For example, in a four-week muscle atrophy study, a composition of ten amino acids, including branched chain amino acids, some essential amino acids, glutamine, arginine, and N-acetyl cysteine (NAC), demonstrated robust effects in attenuating muscle atrophy during one week of limb immobilization (see U.S. patent application Ser. No. 15/847,343, filed Dec. 19, 2017, entitled AMINO ACID COMPOSITIONS AND METHODS FOR THE TREATMENT OF MUSCLE DISEASES AND DISORDERS). This unique composition also demonstrated improved muscle health and strength, even with a brief recovery period following immobilization, and favorably impacted systemic inflammation by simultaneously boosting anti-inflammatory cytokines while suppressing pro-inflammatory mediators.

Another composition, comprising the branched chain amino acids, arginine, glutamine, and NAC, produced clinically meaningful improvements in the overall metabolic profile of patients, including the lowering of hepatic steatosis by simultaneously impacting multiple drivers of non-alcoholic fatty liver disease (NAFLD) in a study of patients with type 2 diabetes and NAFLD (see U.S. patent application Ser. No. 15/847,289, filed Dec. 19, 2017, entitled AMINO ACID COMPOSITIONS AND METHODS FOR THE TREATMENT OF LIVER DISEASES). Administration of the composition also increased markers of insulin sensitivity, decreased lipotoxicity, decreased the level of markers of inflammation and apoptosis, and suppressed fibrogenic markers.

Many amino acids, including histidine, leucine, isoleucine, phenylalanine, arginine, and tryptophan have an unpleasant bitter taste. Lecithin is one excipient that has been used to mask bitter taste, as well as provide wetting properties, but lecithin at high doses has undesired physiological effects. Accordingly, there is a need in the art for compositions comprising bitter tasting amino acids, and particularly pharmaceutical compositions containing bitter tasting amino acids, to have acceptable taste characteristics, preferably without using lecithin.

SUMMARY

Provided herein is an excipient formulation that provides for masking bitterness of compositions comprising at least three amino acid entities (herein an Active Moiety), at least one of which has bitter taste characteristics. In one aspect, the compositions meet a pharmaceutically accepted standard and are pharmaceutical grade dry blended preparations (PGDBP).

In one aspect, the invention is directed to a composition of at least three amino acid entities and an excipient formulation, which composition is suitable for oral administration, wherein the composition has an acceptable taste, and wherein the excipient formulation has fewer than eleven (11) ingredients.

In some embodiments, the invention is directed to a composition comprising at least three amino acids entities and an excipient formulation, which composition is suitable for oral administration, wherein at least one amino acid entity has a bitter taste and the composition has an acceptable taste, wherein the excipient formulation has fewer than eleven (11) ingredients, and wherein: the bitter tasting amino acid is arginine, the composition comprises a rapid onset sweetener, e.g., acesulfame, at a level less than 1% (w/w) (optionally, comprising no rapid onset sweetener, e.g., acesulfame), or the excipient comprises a sweetener, e.g., sucralose, at a level less than 3.9% (w/w) (optionally, at least 0.05%). In some embodiments, the invention is directed to a composition comprising at least three amino acids entities and an excipient formulation, which composition is suitable for oral administration, wherein at least one amino acid entity has a bitter taste and the composition has an acceptable taste, wherein the excipient formulation has fewer than eleven (11) ingredients, and wherein: the bitter tasting amino acid is arginine, the composition comprises a rapid onset sweetener, e.g., acesulfame, at a level less than 1% (w/w) (optionally, comprising no rapid onset sweetener, e.g., acesulfame), and the excipient comprises a sweetener, e.g., sucralose, at a level less than 3.9% (w/w) (optionally, at least 0.05%).

Usually in such a composition at least one amino acid entity has a bitter taste. Exemplary bitter tasting amino acid entities include histidine, leucine, isoleucine, valine, arginine, tryptophan, and phenylalanine. Thus, in a composition of the invention a bitter tasting amino acid entity can be histidine, leucine, isoleucine, valine, arginine, tryptophan, or phenylalanine. Some compositions will contain more than one bitter tasting amino acid entity. For example, a composition may comprise the following groups of amino acids, some or which are bitter tasting: (i) leucine, isoleucine, valine, lysine, histidine, threonine, and L-ornithing-L-aspartate; (ii) leucine, isoleucine, valine, acetylcysteine (NAC), and acetyl-L-carnitine (ALCAR); (iii) leucine, isoleucine, valine, arginine, glutamine, NAC, histidine, lysine, phenylalanine, and threonine; and (iv) leucine, isoleucine, valine, arginine, and NAC.

Exemplary Active Moieties include an Active Moiety useful for treating muscle atrophy and other diseases and disorders of muscle and containing leucine, isoleucine, valine, arginine, N-acetylcystein (NAC), histidine, lysine, phenylalanine, and threonine, of which leucine, isoleucine, valine, arginine, histidine, and phenylalanine taste bitter. Another Active Moiety useful for treating liver diseases and disorders contains leucine, isoleucine, valine, arginine, and N-acetylcystein (NAC), of which all but NAC taste bitter. Exemplified herein are two additional Active Moieties: one for treatment of cirrhosis and containing leucine, isoleucine, valine, lysine, histidine, threonine, and L-ornithine-L-aspartate, of which leucine, isoleucine, valine, and histidine taste bitter; and one for treatment of traumatic brain injury and containing leucine, isoleucine, valine, N-acetylcystein (NAC), and acetyl-L-carnitine (ALCAR), of which leucine, isoleucine, and valine taste bitter.

An advantage of the excipient formulations of this invention is that they omit ingredients thought to be useful or advantageous for compositions comprising a bitter tasting amino acid entity. Thus, a composition of can be free of lecithin. Alternatively, a composition can be free of a bitterness masking agent. A composition can be free of a rapid onset sweetener, such as Acesulfame Potassium (Acesulfame K).

The excipient formulation of the invention may comprise a a sweetener, e.g., sucralose. It may comprise a thickening agent, e.g., Xanthan Gum. It may comprise a pH modifying agent, and more particularly an acidic pH modifying agent, such as citric acid. It may comprise a single flavor agent, more particularly a citrus flavor agent, e.g., an orange flavor, such as natural and with other natural flavors (WONF) orange. It may comprise an aroma flavor agent, e.g., vanilla custard. And the composition of the invention may comprise a coloring agent (colorant), e.g., an orange coloring agent such as FD&C Yellow No. 6. As exemplified herein, all of the foregoing excipient ingredients can be found together, e.g., the excipient formulation comprises a sweetener, a thickening agent, a pH modifying agent, a single flavor agent, an aroma flavor agent, and a coloring agent. Alternatively, the excipient formulation consists of a sweetener, a thickening agent, a pH modifying agent, a single flavor agent, an aroma flavor agent, and a coloring agent, i.e., the excipient formulation has only six (6) ingredients. In each case, the sweetener can be sucralose, the thickening agent can be Xanthan Gum, the pH modifying agent can be an acid, e.g., citric acid, the flavor agent can be a citrus flavor such as orange, e.g., natural and WONF orange, the aroma flavor agent can be vanilla custard, and the coloring agent can be orange, e.g., FD&C Yellow No. 6. Each of the foregoing excipient formulations can be free of one, two, or all three of lecithin, a bitterness masking agent, or a rapid onset sweetener, e.g., Acesulfame K. alternatively, each of the foregoing excipient formulations can contain a one or two of lecithin (though preferably not lecithin), a bitterness masking agent, or a rapid onset sweetener, e.g., Acesulfame K.

In a specific example, the excipient formulation comprises sucralose, Xanthan Gum, an acid for modifying pH, e.g., citric acid, a single citrus flavor agent, e.g., orange, a vanilla custard aroma flavor agent, and an orange coloring agent, e.g., FD&C Yellow No. 6. More particularly, the excipient formulation consists of sucralose, Xanthan Gum, an acid for modifying pH, e.g., citric acid, a single citrus flavor agent, e.g. orange, a vanilla custard aroma flavor agent, and an orange coloring agent, e.g., FD&C Yellow No. 6. Each of the foregoing excipient formulations can be free of one, two, or all three of lecithin, a bitterness masking agent, or a rapid onset sweetener, e.g., Acesulfame K.

The excipient may be less than about 30% of the composition by weight, more particularly less than about 25% of the composition by weight, still more particularly less than about 20% of the composition by weight, and as shown in the Examples, less than about 18% of the composition by weight.

BRIEF DESCRIPTION OF THE FIGURES

FIG. 1 shows Table 17, listing formulation details of exemplary samples.

FIG. 2 shows Table 18, listing intensity scores for attributes of exemplary samples.

FIG. 3 shows Table 19, listing DOD scores over time for exemplary samples.

FIG. 4 shows Table 20, listing DOD scores over time for exemplary samples.

DETAILED DESCRIPTION

The present invention is based on the unprecedented discovery that compositions comprising amino acid entities are capable of significant therapeutic effect. The most convenient way to administer these compositions is orally, thus an important co-extensive discovery is an effective excipient formulation to mask the bitter taste of certain amino acids.

There are various methods to determine flavor of a product or preparation. Organoleptic testing can be applied to any tastes, e.g., sweet, sour, spicy (hot), and bitterness. In one example, a human tasting panel evaluate flavor or taste of a substance. More precise and less subjective tests for most properties, ranging from chemical to electronic. For example, bitterness can be tested with devices such as the Alpha MOS ASTREE Electronic Tongue, which is more repeatable than a sensory panel and is often used for testing the bitterness level of drugs.

The present invention provides, at least in part, dry blended preparations of a plurality of amino acid entities—at least three amino acid entities. In further embodiments, the dry blended preparation, e.g., PGDBP, comprises at least four different amino acid entities.

The excipient composition strategy addresses requirements for wetting, stabilizing/thickening, color, taste and odor masking. An initial formulation, containing eleven (11) different components, provided a consistent "orange creamsicle" flavor. It has now been found that fewer excipients are required for the Active Moiety compositions of amino acids that have physiological activity. In particular, it was found possible to reduce the number of excipient components to avoid redundancy; avoid excipients that have metabolic activity in high doses (e.g., lecithin) even though they have other important functions, e.g., wetting; eliminate excipients that interfere with analytical testing, e.g., because they reduce HPLC column life.

Moreover, the new excipient formulations still provide a standardized flavor, such as the exemplified orange creamsicle flavor. Despite the reduction in number of components in the excipient formulation, the formulation can be modified depending on the target patient population (e.g., a different color/taste profile can be created for children).

The PGDBP is capable of treating or ameliorating one or more of: decreased muscle function due to aging, injury, atrophy, infection, or disease; muscle atrophy; sarcopenia, e.g., cirrhotic sarcopenia; muscle deterioration; muscle decay; cachexia; drug-induced myopathy; muscular dystrophy; myopenia; traumatic brain injury (TBI); chronic traumatic encephalopathy; decreased neuronal signaling; increased inflammation of brain tissue; increased microglial response to pro-inflammatory signals; decreased ionic flux; decreased mitochondrial function; TCA cycle anaplerosis; increased synaptic dysfunction; decreased fat metabolism; hepatocyte apoptosis; hepatocyte ballooning; inflammation of adipose tissue; inflammation of hepatic tissue; fibrosis; liver injury; glucose tolerance; oxidative stress; non-alcoholic fatty liver disease (NAFLD); pediatric NAFLD; steatosis, non-alcoholic steatohepatitis (NASH); fibrosis; immobilization; malnutrition; fasting; aging; autophagy; reduced protein synthesis; anabolic resistance; junction integrity; insulin resistance; decreased mitochondrial biogenesis; decreased myogenesis or myotube growth; end stage liver disease (ESLD); hepatic insufficiency; hyperammonemia; ammonia toxicity; decreased urea synthesis;

muscle wasting; ascites; frailty; hepatic encephalopathy; coagulopathy; or an energy deficit.

Definitions

Terms used in the claims and specification are defined as set forth below unless otherwise specified.

It must be noted that, as used in the specification and the appended claims, the singular forms "a," "an" and "the" include plural referents unless the context clearly dictates otherwise.

The terms "taste bitter" or "have a bitter taste" and the like mean that the compound or a composition have the organoleptic property of activating bitter taste receptors.

The term "an acceptable taste" or "an acceptable flavor" means that a composition is palatable to most humans, i.e., its organoleptic properties are not offensive to most humans. In a specific embodiment, such a taste will not significantly interfere with or discourage compliance with taking the composition as a therapy or supplement.

As used herein, the term "Active Moiety" means a combination comprising three or more amino acid entities, typically pharmaceutical grade amino acid entities, that, in aggregate, have the ability to have a physiological effect, and at an effective dose may have a therapeutic effect. For example, an Active Moiety can rebalance a metabolic dysfunction in a subject suffering from a disease or disorder. An Active Moiety can contain other biologically active ingredients. In some examples, the Active Moiety comprises a defined combination of amino acid entities, e.g., as set out in detail below. In other embodiments, the Active Moiety consists of a defined combination of amino acid entities, e.g., as set out in detail below. The individual amino acid entities are present in the Active Moiety in various amounts or ratios, which can be described as amount by weight (e.g., in grams), ratio by weight of amino acid moieties to each other, amount by mole, amount by weight percent of the Active Moiety, amount by mole percent of the Active Moiety, caloric content, percent caloric contribution to the Active Moiety, etc. Generally, this disclosure will provide grams of amino acid entity in a dosage form, weight percent of an amino acid moiety relative to the weight of the Active Moiety, i.e., the weight of all the amino acid moieties and any other biologically active ingredient present in the Active Moiety, or in ratios.

U.S. patent application Ser. No. 15/847,343, filed Dec. 19, 2017, entitled AMINO ACID COMPOSITIONS AND METHODS FOR THE TREATMENT OF MUSCLE DISEASES AND DISORDERS, U.S. patent application Ser. No. 15/847,289, filed Dec. 19, 2017, entitled AMINO ACID COMPOSITIONS AND METHODS FOR THE TREATMENT OF LIVER DISEASES, and U.S. Patent Application Ser. No. 62/614,214, filed Jan. 5, 2018, entitled AMINO ACID COMPOSITIONS AND METHODS FOR THE TREATMENT OF LIVER DISEASES AND DISORDERS ASSOCIATED WITH HYPERAMMONEMIA, each of which is specifically incorporated herein by reference in its entirety, disclose compositions of amino acid entities, i.e., Active Moieties.

As used herein, the term "amino acid entity" refers to an amino acid in one or both of free form or salt form, an amino acid residue of a peptide (e.g., of a dipeptide, oligopeptide, or polypeptide), a derivative of an amino acid, a precursor of an amino acid, or a metabolite of an amino acid. In some embodiments, an amino acid entity may be part of a peptide no longer than 20 amino acids long. In some embodiments, the derivative of an amino acid entity comprises an amino acid ester (e.g., an alkyl ester, e.g., an ethyl ester or a methyl ester of an amino acid entity) or a keto-acid.

TABLE 1

Amino acid entities include amino acids, precursors, metabolites, and derivatives of the compositions described herein.

| | Exemplary Amino Acid | Precursors | Metabolites | Derivatives |
|---|---|---|---|---|
| L | L-Leucine | Oxo-leucine | HMB (beta-hydroxy-beta-methyl butyrate); Oxo-leucine; Isovaleryl-CoA | D-Leucine; N-Acetyl-Leucine |
| I | L-Isoleucine | 2-Oxo-3-methyl-valerate; Threonine | 2-Oxo-3-methyl-valerate; Methylbutyrl-CoA | D-Isoleucine; N-Acetyl-Isoleucine |
| V | L-Valine | 2-Oxo-valerate | Isobutryl-CoA; 3-HIB-CoA; 3-HIB | D-Valine; N-Acetyl-Valine |
| R | L-Arginine | Argininosuccinate; Citrulline; Aspartate; Glutamate | Ornithine; Citrulline; Agmatine; Creatine | D-Arginine; N-Acetyl-Arginine; |
| Q | L-Glutamine | Glutamate | Carbamoyl-P; Glutamate | D-Glutamine; N-Acetyl-Glutamine; |
| NAC | N-Acetylcysteine | Serine; Acetylserine; Cystathionine; | Glutathione; Cystathionine; Homocysteine; Methionine | D-Cysteine; L-Cysteine; Cystine; Cysteamine |
| H | L-Histidine | Histidinol; Histidinal; Ribose-5-phosphate | Carnosine; Histamine; Urocanate | D-Histidine; N-Acetyl-Histidine |
| K | L-Lysine | Diaminopimelate; Aspartate | Trimethyllysine; Carnitine; Saccharopine | D-Lysine; N-Acetyl-Lysine |
| F | L-Phenylalanine | Phenylpyruvate | Tyrosine | D-Phenylalanine; N-Acetyl-Phenylalanine |

TABLE 1-continued

Amino acid entities include amino acids, precursors, metabolites, and derivatives of the compositions described herein.

| | Exemplary Amino Acid | Precursors | Metabolites | Derivatives |
|---|---|---|---|---|
| T | L-Threonine | Homoserine; O-PhosphoHomoserine | Oxobutyrate | D-Threonine; N-Acetyl-Threonine |
| S | L-Serine | Phosphoserine, P-hydroxypyruvate, L-Glycine | Glycine, Tryptophan, Acetylserine, Cystathionine, Phosphatidylserine | |

As used herein the term "XXX amino acid entity" refers to an amino acid entity that if a free amino acid, comprises free XXX or XXX in salt form; if a peptide, refers to a peptide comprising an XXX residue; if a derivative, refers to a derivative of XXX; if a precursor, refers to a precursor of XXX; and if a metabolite, refers to a XXX metabolite. For example, where XXX is leucine (L), then L-amino acid entity refers to free L or L in salt form, a peptide comprising a L residue, a L derivative, a L precursor, or a metabolite of L; where XXX is arginine (R), then R-amino acid entity refers to free R or R in salt form, a peptide comprising a R residue, a R derivative, a R precursor, or a metabolite of R; where XXX is glutamine (Q), then Q-amino acid entity refers to free Q or Q in salt form, a peptide comprising a Q residue, a Q derivative, a Q precursor, or a metabolite of Q; where XXX is N-acetylcysteine (NAC), then NAC-amino acid entity refers to free NAC or NAC in salt form, a peptide comprising a NAC residue, a NAC derivative, a NAC precursor, or a metabolite of NAC; where XXX is histidine (H), then H-amino acid entity refers to free H or H in salt form, a peptide comprising a H residue, a H derivative, a H precursor, or a metabolite of H; where XXX is lysine (K), then K-amino acid entity refers to free K or K in salt form, a peptide comprising a K residue, a K derivative, a K precursor, or a metabolite of K; where XXX is phenylalanine (F), then F-amino acid entity refers to free F or F in salt form, a peptide comprising a F residue, a F derivative, a F precursor, or a metabolite of F; or where XXX is threonine (T), then T-amino acid entity refers to free T or T in salt form, a peptide comprising a T residue, a T derivative, a T precursor, or a metabolite of T.

Amino acid entities optionally do not include peptides larger than 20 amino acids, such as naturally occurring polypeptides and proteins, in whole or modified, e.g., hydrolyzed form. Active Moieties and pharmaceutical compositions do not include whey, casein, lactalbumin, and other proteins, e.g., found in nutritional supplement or enteric preparations, whether in intact protein form or hydrolyzed form. Amino acid entities include metabolites and derivatives that are capable of effecting biological functionality of the free L-amino acid.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

An "amino acid" refers to an organic compound having an amino group ($-NH_2$), a carboxylic acid group ($-C(=O)OH$), and a side chain bonded through a central carbon atom, and includes essential and non-amino acids, as well as natural and unnatural amino acids.

The proteogenic amino acids, shown below, are known by three- and one-letter abbreviations in addition to their full names. For a given amino acid, these abbreviations are used interchangeably herein. For example, Leu, L or leucine all refer to the amino acid leucine; Ile, I or isoleucine all refer to the amino acid isoleucine; Val, V or valine all refer to the amino acid valine; Arg, R or arginine all refer to the amino acid arginine; and Gln, Q or glutamine all refer to the amino acid glutamine. Likewise, the non-natural amino acid derivative N-acetylcysteine may be referred to interchangeably by "NAC" or "N-acetylcysteine." Amino acids may be present as D- or L-isomers. Unless otherwise indicated, amino acids referred to herein are L-isomers of amino acids.

TABLE 2

Amino acid names and abbreviations

| Amino acid | Three-letter | One-letter |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "branched chain amino acid" is an amino acid selected from leucine, isoleucine, and valine.

The term "effective amount" as used herein means an amount of an Active Moiety which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of treatment, the nature of concurrent therapy, the particular active ingredient(s) being employed, the particular pharmaceutically-acceptable excipient(s) and/or carrier(s) utilized, and like factors with the knowledge and expertise of the attending physician.

A dry blended preparation, e.g., PGDBP, described herein may be formulated as a "pharmaceutical composition". A pharmaceutical composition as described herein comprises at least one amino acid entity and a pharmaceutically acceptable carrier or excipient. In some embodiments, the pharmaceutical composition is used as a therapeutic or a medical food. In some embodiments, the pharmaceutical composition is used as a nutriceutical or as a supplement.

The term "pharmaceutical grade" as used herein, refers to amino acids, materials, excipients, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments, pharmaceutical grade means that the amino acids, materials, or excipients meet the specifications of a monograph, e.g., a monograph of the United States Pharmacopeia (USP), the National Formulary (NF), British Pharmacopeia (BP), European Pharmacopeia (EP), or Japanese Pharmacopeia (JP) detailing tests and acceptance criteria. In some embodiments, the meaning of pharmaceutical grade comprises that the amino acids, excipients, or materials are at least 99% pure.

A dry blended preparation, as used herein, means a combination of a plurality of amino acid entities that substantially lacks water. In some embodiments, a dry blended preparation is a powder. In some embodiments, a dry blended preparation comprises less than or equal to 10, 9, 8, 7, 6, 5, 4, 3, 2, or 1% water by weight. In some embodiments, a dry blended preparation comprises at least 4 amino acid entities, e.g., 4, 5, 6, 7, 8, 9, 10, 11, 12, 13, 14, 15, 16, 17, 18, 19, or 20 amino acid entities.

A pharmaceutical grade dry blended preparation (PGDBP), as used herein, is a dry blended preparation that meets a reference standard (e.g., one or more reference standards) and comprises a plurality of pharmaceutical grade amino acid entities. A PGDBP may be formulated as a pharmaceutical composition, e.g., the PGDBP may further comprise one or more excipients and/or oral administration components. In some embodiments, a reference standard met by a PGDBP is composition uniformity.

A reference standard, as used herein, means: a standard used or set by:

(1) a manufacturer of a combination (e.g., dry blended preparation, e.g., PGDBP), e.g., a manufacturer having approval from a governmental agency to market the PGDBP, or (2) the pharmaceutical industry or agencies or entities (e.g., government or trade agencies or entities) regulating the pharmaceutical industry, to ensure one or more product quality parameters are within acceptable ranges for a medicine, pharmaceutical composition, treatment, or other therapeutic. A product quality parameter can be any parameter regulated by the manufacturer, pharmaceutical industry or by agencies or entities, e.g., government or trade agencies or entities, including but not limited to composition; composition uniformity; dosage; dosage uniformity; presence, absence, and/or level of contaminants or impurities; and level of sterility (e.g., the presence, absence and/or level of microbes). Exemplary government regulatory agencies include: Federal Drug Administration (FDA), European Medicines Agency (EMA), SwissMedic, China Food and Drug Administration (CFDA), or Japanese Pharmaceuticals and Medical Devices Agency (PMDA), Health Canada, and Medicines and Healthcare Products Regulatory Agency (MHRA). A product quality parameter can also be a parameter specified by a national or regional pharmacopeia or formulary, including the U.S. Pharmacopeia (USP), British Pharmacopeia (BP), National Formulary (NF), European Pharmacopeia (EP), or Japanese Pharmacopeia (JP).

Composition uniformity, as used herein, is a standard for the homogeneity of a component of a combination, e.g., a dry blended preparation, e.g., a PGDBP, that comprises blend uniformity, portion uniformity, or both. In some embodiments, a combination meets a standard for composition uniformity, e.g., blend uniformity, if the amount of a component (e.g., a pharmaceutical grade amino acid entity, excipient, or oral administration component) at a sampling point in the combination differs from a reference value by less than a predetermined amount. In some embodiments, the reference value is the amount of the component at a second sampling point in the combination. In some embodiments, the reference value is the amount of the component (e.g., a pharmaceutical grade amino acid entity, excipient, or oral administration component) present in the combination (e.g., a dry blended preparation, e.g., a PGDBP).

In some embodiments, wherein a combination (e.g., a dry blended preparation, e.g., a PGDBP) is divided into portions, the portions of the combination meet a standard for composition uniformity, e.g., portion uniformity, if the amount of a component (e.g., a pharmaceutical grade amino acid entity, excipient, or oral administration component) in a portion differs from a reference value by less than a predetermined amount. In some embodiments, the reference value is the amount of the component in a second portion. In some embodiments, the reference value comprises the amount of the component in a N additional portions, wherein in is at least 2, 3, 4, 5, 6, 7, 8, 9, 10, 20, 30, 40, 50, 60, 70, 80, 90, or 100. In some embodiments, the reference value is the amount of the component (e.g., a pharmaceutical grade amino acid entity, excipient, or oral administration component) present in the combination (e.g., a dry blended preparation, e.g., a PGDBP). Amounts may be absolute (e.g., mass or weight) or relative (e.g., percent of total components). In some embodiments, the predetermined amount may be 20, 19, 18, 17, 16, 15, 14, 13, 12, 11, 10, 9, 8, 7, 6, 5, 4, 3, 2, or 1%, e.g., of the reference value. In some embodiments, the predetermined amount is 10% (e.g., the amount of the component differs from the reference value by less than 10%).

A composition, formulation or product is "therapeutic" if it provides a beneficial clinical effect, i.e., a therapeutic effect, when administered to a subject, e.g., patient. A beneficial clinical effect, i.e., therapeutic effect, may comprise lessening the progression of a disease or condition and/or alleviating one or more symptoms of the disease or condition. A beneficial clinical effect, i.e., therapeutic effect, may comprise lessening or alleviating side effects associated with another therapy.

A "unit dose" or "unit dosage" as used herein means an amount or dose of medicine prepared in an individual packet or container for convenience, safety, or monitoring. A "unit dose" or "unit dosage" comprises the drug product or drug products in the form in which they are marketed for use, with a specific mixture of active ingredients and inactive components (excipients), in a particular configuration (such as a capsule shell, for example), and apportioned into a particular dose.

A "stick pack" as used herein means a flexible disposable or single use container comprising a unit dosage of PGDBP. In some embodiments, the container is plastic, paper, or thermoplastic polymer resin, e.g., tearable plastic, paper, or thermoplastic polymer resin. In some embodiments, a stick pack comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 g of PGDBP.

Portioning, as used herein, means dividing all or part of the dry blended preparation, e.g., PGDBP, into portions for administration to a patient or subject. The portions created by portioning may be provided in sachets, vials, or other containers, e.g., stick packs. In one embodiment, the portions created by portioning are unit dosage amounts, e.g., one unit dosage or a fraction of a unit dosage (e.g., a stick pack may comprise half a unit dose, such that two stick packs would be used together to provide a single unit dose). In some embodiments, only PGDBPs (e.g., that meet a reference standard) are separated into portions via portioning. In some embodiments, portions generated by portioning also meet a reference standard.

As used herein, the terms "treat," "treating," or "treatment" refer in one embodiment, to ameliorating, e.g., decreased muscle function (e.g., relative to a health subject), a muscle disease, or a muscle disorder (i.e., slowing or arresting or reducing the development of the disease or disorder or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating a symptom of decreased muscle function (e.g., relative to a health subject), a muscle disease, or a muscle disorder, either physically, (e.g., stabilization of a discernible symptom), physiologically, (e.g., stabilization of a physical parameter), or both. In yet another embodiment, "treat," "treating," or "treatment" refers to preventing or delaying the onset or development or progression of decreased muscle function (e.g., relative to a health subject), a muscle disease, or a muscle disorder.

Compositions Comprising Amino Acid Entities

It has been discovered that mixtures of amino acids and related molecules (e.g., combinations, e.g., dry blended preparations, e.g., PGDBPs, of the present disclosure) can treat various disease states by rebalancing patients' metabolic state to address serious unmet medical needs. These endogenous metabolic modulators treat the multifactorial etiology of serious diseases by reprogramming disordered metabolism in an unprecedented, coordinated, multifactorial manner.

The composition of the invention as described herein (e.g., an Active Moiety) comprises amino acid entities, e.g., the amino acid entities shown in Table 1. U.S. patent application Ser. No. 15/847,343, filed Dec. 19, 2017, entitled AMINO ACID COMPOSITIONS AND METHODS FOR THE TREATMENT OF MUSCLE DISEASES AND DISORDERS, U.S. patent application Ser. No. 15/847,289, filed Dec. 19, 2017, entitled AMINO ACID COMPOSITIONS AND METHODS FOR THE TREATMENT OF LIVER DISEASES, and U.S. Patent Application Ser. No. 62/614,214, filed Jan. 5, 2018, entitled AMINO ACID COMPOSITIONS AND METHODS FOR THE TREATMENT OF LIVER DISEASES AND DISORDERS ASSOCIATED WITH HYPERAMMONEMIA, each of which is specifically incorporated herein by reference in its entirety, disclose compositions of amino acid entities, i.e., Active Moieties.

For example, in a four-week muscle atrophy study, a composition of ten amino acids entities, including branched chain amino acids, some essential amino acids, glutamine, arginine, and N-acetyl cysteine (NAC), demonstrated robust effects in attenuating muscle atrophy during one week of limb immobilization (U.S. patent application Ser. No. 15/847,343). This unique composition also demonstrated improved muscle health and strength, even with a brief recovery period following immobilization, and favorably impacted systemic inflammation by simultaneously boosting anti-inflammatory cytokines while suppressing pro-inflammatory mediators. In some embodiments, the methods described herein can be used to produce PGDBPs comprising the amino acid entities described in U.S. patent application Ser. No. 15/847,343, which is hereby incorporated by reference in its entirety. In some embodiments, the PGDBPs, plurality of portions of PGDBPs, or dosage forms described herein comprise the mixtures of amino acid entities described in U.S. patent application Ser. No. 15/847,343.

Another composition, comprising the branched chain amino acids, arginine, glutamine, and NAC, produced clinically meaningful improvements in the overall metabolic profile of patients, including the lowering of hepatic steatosis by simultaneously impacting multiple drivers of non-alcoholic fatty liver disease (NAFLD) in a study of patients with type 2 diabetes and NAFLD (see U.S. patent application Ser. No. 15/847,289). Administration of the composition also increased markers of insulin sensitivity, decreased lipotoxicity, decreased the level of markers of inflammation and apoptosis, and suppressed fibrogenic markers. In some embodiments, the methods described herein can be used to produce PGDBPs comprising the amino acid entities described in U.S. patent application Ser. No. 15/847,289, which is hereby incorporated by reference in its entirety. In some embodiments, the PGDBPs, plurality of portions of PGDBPs, or dosage forms described herein comprise the mixtures of amino acid entities described in U.S. patent application Ser. No. 15/847,289.

The present disclosure provides compositions, e.g., dry blended preparations, e.g., PGDBPs, comprising amino acid entities. These compositions are made up of pharmaceutical grade amino acid entities including amino acids in one or both of free form or salt form, amino acid residues of a peptide (e.g., of a dipeptide, oligopeptide, or polypeptide), derivatives of an amino acid, precursors of an amino acid, or metabolites of an amino acid.

An exemplary composition includes leucine, isoleucine, valine, arginine HCl, glutamine, N-acetylcysteine, histidine, lysine, phenylalanine, and threonine as its defined amino acid components in a wt. ratio of 2.0:1.0:1.0:3.62:2.66:0.3:0.16:0.7:0.16:0.34 (Table 3). The Amino Acid Composition includes leucine, isoleucine, valine, arginine, glutamine, N-acetylcysteine, histidine, lysine, phenylalanine, and threonine as its defined amino acid components in a wt. ratio of 2.0:1.0:1.0:3.0:2.66:0.3:0.16:0.7:0.16:0.34.

An exemplary dry blended preparation, e.g., PGDBP, includes leucine, isoleucine, valine, arginine HCl, glutamine, N-acetylcysteine, histidine, lysine, phenylalanine, and threonine as its defined amino acid components in a wt. ratio of 2.0:1.0:1.0:3.62:2.66:0.3:0.16:0.7:0.16:0.34 (Table 3). The dry blended preparation, e.g., PGDBP, includes leucine, isoleucine, valine, arginine, glutamine, N-acetylcysteine, histidine, lysine, phenylalanine, and threonine as its defined amino acid components in a wt. ratio of 2.0:1.0:1.0:3.0:2.66:0.3:0.16:0.7:0.16:0.34.

TABLE 3

Exemplary amino acid components of the composition.

| Amino acid | weight ratio | g/packet | g/dose 1 | Total g daily dose 1 | g/dose 2 | Total g daily dose 2 |
|---|---|---|---|---|---|---|
| Leucine | 2.0 | 1.0 | 1.0 | 3 | 4 | 12 |
| Isoleucine | 1.0 | 0.5 | 0.5 | 1.5 | 2 | 6 |
| Valine | 1.0 | 0.5 | 0.5 | 1.5 | 2 | 6 |
| Arginine HCl | 3.62 | 1.81 | 1.81 | 5.43 | 7.24 | 21.72 |
| Glutamine | 2.66 | 1.33 | 1.33 | 3.99 | 5.32 | 15.96 |
| N-acetyl-cysteine | 0.3 | 0.15 | 0.15 | 0.45 | 0.6 | 1.8 |
| Histidine | 0.16 | 0.08 | 0.08 | 0.24 | 0.32 | 0.96 |
| Lysine | 0.7 | 0.35 | 0.35 | 1.05 | 1.4 | 4.2 |
| Phenylalanine | 0.16 | 0.08 | 0.08 | 0.24 | 0.32 | 0.96 |
| Threonine | 0.34 | 0.17 | 0.17 | 0.51 | 0.68 | 2.04 |
| Total amino acids | | ~6 g | ~6 g | ~18 g | ~24 g | ~72 g |

An exemplary Amino Acid Composition includes leucine, isoleucine, valine, arginine HCl, glutamine, and N-acetylcysteine as its amino acid entities in a wt. ratio of 1:0.5:0.5:1.81:2:0.15 (Table 4). An exemplary dry blended preparation, e.g., PGDBP, includes leucine, isoleucine, valine, arginine, glutamine, and N-acetylcysteine as its amino acid entities in a wt. ratio of 1:0.5:0.5:1.5:2:0.15 (Table 5).

TABLE 4

Exemplary amino acid components of the composition including Arginine HCl

| Amino acid | wt. ratio | wt. % | g/packet | g dose #1 | g dose #2 |
|---|---|---|---|---|---|
| Leucine | 1 | 16.78 | 1.00 g | 2 g | 4 g |
| Isoleucine | 0.5 | 8.39 | 0.50 g | 1 g | 2 g |
| Valine | 0.5 | 8.39 | 0.50 g | 1 g | 2 g |
| Arginine HCl | 1.81 | 30.37 | 1.81 g | 3.62 g | 7.24 g |
| Glutamine | 2 | 33.56 | 2.00 g | 4 g | 8 g |
| N-acetylcysteine | 0.15 | 2.52 | 0.15 g | 0.3 g | 0.6 g |
| Total amino acids | | | 5.96 g | ~12 g | ~24 g |

TABLE 5

Exemplary amino acid components of the composition including Arginine.

| Amino acid | wt. ratio | wt. % | g/packet | g dose #1 | g dose #2 |
|---|---|---|---|---|---|
| Leucine | 1 | 17.70 | 1.00 g | 2 | 4 |
| Isoleucine | 0.5 | 8.85 | 0.50 g | 1 | 2 |
| Valine | 0.5 | 8.85 | 0.50 g | 1 | 2 |
| Arginine | 1.5 | 26.55 | 1.5 g | 3 | 6 |
| Glutamine | 2 | 35.4 | 2.00 g | 4 | 8 |
| N-acetylcysteine | 0.15 | 2.65 | 0.15 g | 0.3 | 0.6 |
| Total amino acids | | | 5.65 g | 11.3 g | 22.6 g |

An exemplary dry blended preparation, e.g., PGDBP, includes leucine, isoleucine, valine, arginine HCl, glutamine, and N-acetylcysteine as its amino acid entities in a wt. ratio of 1:0.5:0.5:0.905:2:0.15 (Table 6). An exemplary dry blended preparation, e.g., PGDBP, includes leucine, isoleucine, valine, arginine, glutamine, and N-acetylcysteine as its amino acid entities in a wt. ratio of 1:0.5:0.5:0.75:2:0.15 (Table 7).

TABLE 6

Exemplary amino acid components of the composition including Arginine HCl.

| Amino acid | wt. ratio | wt. % | g/packet | g dose #1 | g dose #2 |
|---|---|---|---|---|---|
| Leucine | 1 | 19.78 | 1.00 g | 2 g | 4 g |
| Isoleucine | 0.5 | 9.89 | 0.50 g | 1 g | 2 g |
| Valine | 0.5 | 9.89 | 0.50 g | 1 g | 2 g |
| Arginine HCl | 0.905 | 17.90 | 0.905 g | 1.81 g | 3.62 g |
| Glutamine | 2 | 39.56 | 2.00 g | 4 g | 8 g |
| N-acetylcysteine | 0.15 | 2.97 | 0.15 g | 0.3 g | 0.6 g |
| Total amino acids | | | 5.06 g | ~10 g | ~20 g |

TABLE 7

Exemplary amino acid components of the composition including Arginine.

| Amino acid | wt. ratio | wt. % | g/packet | g dose #1 | g dose #2 |
|---|---|---|---|---|---|
| Leucine | 1 | 20.41 | 1.00 g | 2 | 4 |
| Isoleucine | 0.5 | 10.20 | 0.50 g | 1 | 2 |
| Valine | 0.5 | 10.20 | 0.50 g | 1 | 2 |
| Arginine | 0.75 | 15.31 | 0.75 g | 1.5 | 3 |
| Glutamine | 2 | 40.82 | 2.00 g | 4 | 8 |
| N-acetylcysteine | 0.15 | 3.06 | 0.15 g | 0.3 | 0.6 |
| Total amino acids | | | 4.9 g | 9.8 g | 19.6 g |

An exemplary dry blended preparation, e.g., PGDBP, includes leucine, isoleucine, valine, arginine HCl, glutamine, and N-acetylcysteine as its amino acid entities in a wt. ratio of 1:0.5:0.25:0.905:1:0.225 (Table 8). An exemplary dry blended preparation, e.g., PGDBP, includes leucine, isoleucine, valine, arginine, glutamine, and N-acetylcysteine as its amino acid entities in a wt. ratio of 1:0.5:0.25:0.75:1:0.225 (Table 9).

TABLE 8

Exemplary amino acid components of the composition including Arginine HCl.

| Amino acid | wt. ratio | wt. % | g/packet | g dose #1 | g dose #2 |
|---|---|---|---|---|---|
| Leucine | 1 | 25.77 | 1.00 g | 2 g | 4 g |
| Isoleucine | 0.5 | 12.89 | 0.50 g | 1 g | 2 g |
| Valine | 0.25 | 6.44 | 0.25 g | 0.50 g | 1 g |
| Arginine HCl | 0.905 | 23.32 | 0.905 g | 1.81 g | 3.62 g |
| Glutamine | 1 | 25.77 | 1.00 g | 2 g | 4 g |
| N-acetylcysteine | 0.225 | 5.80 | 0.225 g | 0.45 g | 0.9 g |
| Total amino acids | | | 3.88 g | 7.76 g | 15.52 g |

TABLE 9

Exemplary amino acid components of the composition including Arginine.

| Amino acid | wt. ratio | wt. % | g/packet | g dose #1 | g dose #2 |
|---|---|---|---|---|---|
| Leucine | 1 | 26.85 | 1.00 g | 2 | 4 |
| Isoleucine | 0.5 | 13.42 | 0.50 g | 1 | 2 |
| Valine | 0.25 | 6.71 | 0.25 g | 0.5 | 1 |
| Arginine | 0.75 | 20.13 | 0.75 g | 1.5 | 3 |
| Glutamine | 1 | 26.85 | 1.00 g | 2 | 4 |
| N-acetylcysteine | 0.225 | 6.04 | 0.225 g | 0.45 | 0.9 |
| Total amino acids | | | 3.725 g | 7.45 g | 14.9 g |

An exemplary dry blended preparation, e.g., PGDBP, includes leucine, isoleucine, valine, arginine HCl, glutamine, N-acetylcysteine, and serine as its amino acid entities in a wt. ratio of 1:0.5:0.25:0.905:1:0.225:0.667 (Table 10). An exemplary dry blended preparation, e.g., PGDBP, includes leucine, isoleucine, valine, arginine, glutamine, N-acetylcysteine, and serine as its amino acid entities in a wt. ratio of 1:0.5:0.25:0.75:1:0.225:1.5 (Table 11).

TABLE 10

Exemplary amino acid components of the composition including Arginine HCl.

| Amino acid | wt. ratio | wt. % | g/packet | g dose #1 | g dose #2 |
|---|---|---|---|---|---|
| Leucine | 1 | 18.59 | 1.00 g | 2 g | 4 g |
| Isoleucine | 0.5 | 9.29 | 0.50 g | 1 g | 2 g |
| Valine | 0.25 | 4.65 | 0.25 g | 0.50 g | 1 g |
| Arginine HCl | 0.905 | 16.82 | 0.905 g | 1.81 g | 3.62 g |
| Glutamine | 1 | 18.59 | 1.00 g | 2 g | 4 g |
| N-acetylcysteine | 0.225 | 4.18 | 0.225 g | 0.45 g | 0.9 g |
| Serine | 1.5 | 27.88 | 1.5 | 3 | 6 |
| Total amino acids | | | 5.38 g | 10.76 g | 21.52 g |

TABLE 11

Exemplary amino acid components of the composition including Arginine.

| Amino acid | wt. ratio | wt. % | g/packet | g dose #1 | g dose #2 |
|---|---|---|---|---|---|
| Leucine | 1 | 19.14 | 1.00 g | 2 | 4 |
| Isoleucine | 0.5 | 9.57 | 0.50 g | 1 | 2 |
| Valine | 0.25 | 4.78 | 0.25 g | 0.5 | 1 |
| Arginine | 0.75 | 14.35 | 0.75 g | 1.5 | 3 |
| Glutamine | 1 | 19.14 | 1.00 g | 2 | 4 |
| N-acetylcysteine | 0.225 | 4.31 | 0.225 g | 0.45 | 0.9 |
| Serine | 1.5 | 28.71 | 1.5 | 3 | 6 |
| Total amino acids | | | 5.225 | 10.45 | 20.9 |

An exemplary dry blended preparation, e.g., PGDBP, includes leucine, isoleucine, valine, arginine HCl, glutamine, N-acetylcysteine, and serine as its amino acid entities in a wt. ratio of 1:0.5:0.25:0.905:1:0.225:0.667 (Table 12). An exemplary dry blended preparation, e.g., PGDBP, includes leucine, isoleucine, valine, arginine, glutamine, N-acetylcysteine, and serine as its amino acid entities in a wt. ratio of 1:0.5:0.25:0.75:1:0.225:1.667 (Table 13).

TABLE 12

Exemplary amino acid components of the composition including Arginine HCl.

| Amino acid | wt. ratio | wt. % | g/packet | g dose #1 | g dose #2 |
|---|---|---|---|---|---|
| Leucine | 1 | 18.02 | 1.00 g | 2 g | 4 g |
| Isoleucine | 0.5 | 9.01 | 0.50 g | 1 g | 2 g |
| Valine | 0.25 | 4.50 | 0.25 g | 0.50 g | 1 g |
| Arginine HCl | 0.905 | 16.31 | 0.905 g | 1.81 g | 3.62 g |
| Glutamine | 1 | 18.02 | 1.00 g | 2 g | 4 g |
| N-acetylcysteine | 0.225 | 4.05 | 0.225 g | 0.45 g | 0.9 g |
| Serine | 1.667 | 30.09 | 1.67 g | 3.33 g | 6.67 g |
| Total amino acids | | | 5.55 g | 11.09 g | 22.19 g |

TABLE 13

Exemplary amino acid components of the composition including Arginine.

| Amino acid | wt. ratio | wt. % | g/packet | g dose #1 | g dose #2 |
|---|---|---|---|---|---|
| Leucine | 1 | 18.54 | 1.00 g | 2 | 4 |
| Isoleucine | 0.5 | 9.27 | 0.50 g | 1 | 2 |
| Valine | 0.25 | 4.64 | 0.25 g | 0.5 | 1 |

TABLE 13-continued

Exemplary amino acid components of the composition including Arginine.

| Amino acid | wt. ratio | wt. % | g/packet | g dose #1 | g dose #2 |
|---|---|---|---|---|---|
| Arginine | 0.75 | 13.91 | 0.75 g | 1.5 | 3 |
| Glutamine | 1 | 18.54 | 1.00 g | 2 | 4 |
| N-acetylcysteine | 0.225 | 4.17 | 0.225 g | 0.45 | 0.9 |
| Serine | 1.667 | 30.92 | 1.67 g | 3.33 g | 6.67 g |
| Total amino acids | | | 5.395 g | 10.78 g | 21.57 g |

An exemplary dry blended preparation, e.g., PGDBP, includes leucine, isoleucine, arginine HCl, glutamine, serine, carnitine, and N-acetylcysteine as its amino acid entities in a wt. ratio of 1:0.5:1.6124:0.6667:2.5:0.3333:0.4333 (Table 21).

TABLE 21

Exemplary amino acid components of the composition.

| Amino acid | wt. ratio | wt. % | g/packet | g dose #1 | g dose #2 |
|---|---|---|---|---|---|
| Leucine | 1.0000 | 13.45 | 1.00 g | 4.0000 | 6.0000 |
| Isoleucine | 0.5000 | 6.72 | 0.50 g | 2.0000 | 3.0000 |
| Arginine | 1.6124 | 21.68 | 1.6124 g | 6.4496 | 9.6744 |
| Glutamine | 0.6667 | 8.97 | 0.6667 g | 2.6666 | 4.0000 |
| Serine | 2.5000 | 33.62 | 2.50 g | 10.0000 | 15.0000 |
| Carnitine | 0.3333 | 4.48 | 0.3333 g | 1.3333 | 2.0000 |
| N-acetylcysteine | 0.4333 | 5.83 | 0.4333 g | 1.7333 | 2.6000 |

An exemplary dry blended preparation, e.g., PGDBP, includes leucine, isoleucine, valine, lysine, histidine, threonine, and ornithine-aspartate as its amino acid entities in a wt. ratio of 0.8889:0.4444:0.8889:0.4703:0.3333:0.3333:1.6667 (Table 22).

TABLE 22

Exemplary amino acid components of the composition.

| Amino acid | wt. ratio | wt. % | g/packet | g dose #1 | g dose #2 |
|---|---|---|---|---|---|
| Leucine | 0.8889 | 15.06 | 0.8889 g | 2.6667 | 8.0000 |
| Isoleucine | 0.4444 | 7.53 | 0.4444 g | 1.3333 | 4.0000 |
| Valine | 0.8889 | 15.06 | 0.8889 g | 2.6667 | 8.0000 |
| Lysine | 0.4703 | 7.97 | 0.4703 g | 1.4108 | 4.2323 |
| Histidine | 0.3333 | 5.65 | 0.3333 g | 1.0000 | 3.0000 |
| Threonine | 0.3333 | 5.65 | 0.3333 g | 1.0000 | 3.0000 |
| Ornithine-Aspartate | 1.6667 | 28.23 | 1.6667 g | 5.0000 | 15.0000 |

An exemplary dry blended preparation, e.g., PGDBP, includes leucine, valine, arginine, glutamine, N-acetylcysteine, serine, carnitine, histidine, lysine, and citrulline as its amino acid entities in a wt. ratio of 3.0:1.0:6.0:5.0:1.3:2.5:1.0:1.0:1.5:4.0 (Table 23).

TABLE 23

Exemplary amino acid components of the composition.

| Amino acid | wt. ratio | wt. % | g/packet | g dose #1 |
|---|---|---|---|---|
| Leucine | 3.0 | 11.4 | 1.00 | 6.0 |
| Valine | 1.0 | 3.8 | 0.33 | 2.0 |
| Arginine | 6.0 | 22.8 | 2.00 | 12.0 |
| Glutamine | 5.0 | 19.0 | 1.67 | 10.0 |
| N-acetylcysteine | 1.3 | 4.9 | 0.43 | 2.6 |
| Serine | 2.5 | 9.5 | 0.83 | 5.0 |
| Carnitine | 1.0 | 3.8 | 0.33 | 2.0 |
| Histidine | 1.0 | 3.8 | 0.33 | 2.0 |
| Lysine | 1.5 | 5.7 | 0.50 | 3.0 |
| Citrulline | 4.0 | 15.2 | 1.33 | 8.0 |

Production of Dry Blended Preparations

The methods disclosed herein may be used to manufacture dry blended preparations (e.g., PGDBPs) of pharmaceutical grade amino acids. Amino acids used to make the dry blended preparations may be agglomerated, and/or instantized to aid in dispersal and/or solubilization. In some embodiments, the amino acids used to make the dry blended preparations are not instantized and/or are substantially free of lecithin.

The dry blended preparations of the present disclosure may be made using amino acids and amino acid derivatives from the following sources, or other sources may used: e.g., FUSI-BCAA™ Instantized Blend (L-Leucine, L-Isoleucine and L-Valine in 2:1:1 weight ratio), FUSIL™ Instantized L-Leucine, L-Arginine HCl, L-Glutamine and other amino acids may be obtained from Ajinomoto Co., Inc; N-acetylcysteine may be obtained from Spectrum Chemical.

To produce the dry blended preparations of the instant disclosure, the following general steps may be used: individual pharmaceutical grade amino acid entities (and, optionally, one or more excipients and/or oral administration components), may be combined into a combination and subjected to one or more blending conditions (e.g., blending and mixing). In some embodiments, the blending conditions are continued until the combination meets one or more reference standards. In some embodiments, the resulting PGDBP is divided into a plurality of portions. In some embodiments, at least a percentage of the portions of the plurality of portions also meet one or more reference standards, e.g., the reference standards that the PGDBP met. In some embodiments, at least a percentage of the portions of the plurality of portions meet one or more reference standards.

In some embodiments, the combination, e.g., dry blended preparation, e.g., PGDBP, comprises an excipient formulation comprising a limited number of excipient and/or oral administration component ingredients. In some embodiments, a combination, e.g., dry blended preparation, e.g., PGDBP, comprising an excipient formulation comprising a limited number of excipient and/or oral administration component ingredients exhibits an acceptable taste, e.g., satisfies a reference standard for taste, (e.g., despite utilizing a limited number of excipient and/or oral administration component ingredients). In some embodiments, excipient formulation comprises less than 20, 19, 18, 17, 16, 15, 14, 13, 12, 11, 10, 9, 8, 7, 6, or 5 excipient and/or oral administration component ingredients (and optionally at least 1, 2, 3, 4, 5, 6, 7, or 8 excipient and/or oral administration component ingredients). In some embodiments, the excipient formulation comprises less than 11, 10, 9, or 8 excipient and/or oral administration component ingredients (and optionally at least 1, 2, 3, 4, 5, 6, 7, or 8 excipient and/or oral administration component ingredients).

In some embodiments, the dry blended preparation, e.g., PGDBP, is also a large-scale preparation. Large-scale, as used herein, describes a preparation that is larger (e.g., by weight, mass, or volume) than a reference value. In some embodiments, the reference value is the size of a typical experimental (e.g., non-manufacturing) preparation. In some embodiments, the reference value is 10, 11, 12, 13, 14, or 15 kg. In some embodiments, large-scale preparations comprise at least 25, 30, 40, 50, 60, 70, 80, 90, 100, 120, 140, 160, 180, 200, 300, 400, 500, 600, 700, 800, 900, 1000, 2000, 3000, 4000, 5000, 6000, 7000, 8000, 9000, or 10000 kg. In some embodiments, large-scale preparations comprise no more than 10000, 5000, 1000, 900, 800, 700, 600, 500, 400, or 300 kg. In some embodiments, a large-scale preparation comprises 100-500 kg, 100-400 kg, 100-300, 100-200 kg, 200-300 kg, 200-400 kg, 200-500 kg, 300-400 kg, 300-500 kg, 400-500, or 500-1000 kg.

Formulations

The dry blended preparations, e.g., PGDBPs, of the present disclosure may be formulated in a form suitable for oral use. For example, PGDBPs may be formulated in dry form as a powder, e.g., in a sachet, vial, stick pack, or dispersible powder or granules. In other embodiments, PGDBPs may be formulated in liquid form, e.g., as an aqueous or oily suspension, emulsion, syrup, gel pack, or elixir. In some embodiments, the PGDBP formulated in dry form can be dissolved in an appropriate solvent to provide PGDBP formulated in liquid form. In the same embodiment, the PGDBP may be accompanied by instructions for adding the dry PGDBP to liquid. The dry blended preparations, e.g., PGDBPs, of the present disclosure may be formulated in a form suitable for enteral administration (for example via tube feeding).

The dry blended preparations, e.g., PGDBPs, of the present disclosure may be formulated as a dietary composition, e.g., chosen from a medical food, a functional food, a supplement, or a nutriceutical. The dry blended preparation, e.g., PGDBP, can be for use as a dietary composition, e.g., chosen from a medical food, a functional food, a supplement, or a nutriceutical. In some embodiments, the dietary composition is for use in a method comprising administering the composition to a subject. In some embodiments, the PGDBP may be accompanied by instructions for adding the dry or liquid PGDBP to food to provide a dietary composition, e.g., chosen from a medical food, a functional food, a supplement, or a nutriceutical.

In some embodiments, dry blended preparations, e.g., PGDBPs, formulated in any manner described herein may further be provided as a unit dosage, e.g., a unit dosage comprising an effective amount of PGDBP for treating one or more conditions in a subject (e.g., a human subject or a human patient). In some embodiments, the unit dosage is for use in a method of treating a condition or symptom of a condition. In some embodiments, the methods described herein further comprises identifying a subject with a condition and/or administering a unit dosage of a dry blended preparation, e.g., PGDBP, e.g., a PGDBP described herein.

In some embodiments, the dry blended preparation, e.g., PGDBP, meets a standard for sterility, e.g., a reference standard for sterility. In some embodiments, the standard for sterility is more sterile than the standard of sterility for food. In some embodiments, the standard for sterility is less sterile than the standard of sterility required for parenteral administration.

In some embodiments, a dry blended preparation, e.g., PGDBP, when dissolved in water, has a pH less than or equal to 9, 8.8, 8.6, 8.4, 8.2, 8, 7.8, 7.6, 7.4, 7.2, 7, 6.8, 6.6, 6.4, 6.2, 6, 5.8, 5.6, 5.4, 5.2, 5, 4.8, 4.6, 4.4, 4.2, 4, 3.9, 3.8, 3.7, 3.6, 3.5, 3.4, 3.3, 3.2, 3.1, or 3 (e.g., less than or equal to 9 or 6) (and optionally at least 3, 3.5, or 5). In some embodiments, dissolved in water means dissolving a dry blended preparation, e.g., PGDBP, e.g., a reference quantity (e.g., a stick pack), in a reference volume of water (e.g., at least 15 ml of water and up to 150 ml of water, e.g., 15, 100, or 120 ml of water).

Excipient Formulation Components

The combinations, e.g., dry blended preparations, e.g., PGDBPs, of the present disclosure may comprise one or more oral administration components. Oral administration components are components that improve or modify a parameter of a combination that is important for effective oral administration (e.g., an oral administration quality (e.g., taste, flavor, aroma, texture, mouth feel, color, etc.). Non-limiting examples of suitable oral administration components include a tastant, a bitterness covering agent, flavorants, a sweetener, odor masking agent, a wetting agent, a stabilizing/thickening agent, and a coloring agent.

In some embodiments, the oral administration component comprises a flavorant. Flavorants can be chosen from synthetic flavor oils and flavoring aromatics; natural oils; extracts from plants, leaves, flowers, and fruits; and combinations thereof. In some embodiments, the flavorant is selected from cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In some embodiments, the oral administration component comprises a sweetener. Non-limiting examples of suitable sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; and sugar alcohols such as sorbitol, mannitol, xylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (Acesulfame-K), and sodium and calcium salts thereof.

In some embodiments, the sweetener is a rapid onset sweetener, e.g., acesulfame. In some embodiments, the combinations, e.g., dry blended preparations, e.g., PGDBPs, comprises a rapid onset sweetener, e.g., acesulfame, at a level less than 0.05, 0.1, 0.2, 0.3, 0.4, 0.5, 0.6, 0.7, 0.8, 0.9, 1, 2, 5, or 10% (w/w), e.g., less than 1% (w/w) (and optionally, at least 0.01, 0.1, 0.5, 1, or 2% (w/w)). In some embodiments, the combinations, e.g., dry blended preparations, e.g., PGDBPs, does not comprises a rapid onset sweetener, e.g., acesulfame. In some embodiments, the combinations, e.g., dry blended preparations, e.g., PGDBPs, does not comprises acesulfame.

In some embodiments, the sweetener is a slow onset sweetener, e.g., sucralose. In some embodiments, the combinations, e.g., dry blended preparations, e.g., PGDBPs, comprises a slow onset sweetener, e.g., sucralose, at a level less than 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.2, 1.4, 1.6, 1.8, 2, 2.2, 2.4, 2.6, 2.8, 3, 3.2, 3.4, 3.6, 3.8, or 3.9% (w/w) (optionally, comprising at least 0.05, 0.1, 0.15, 0.2, 0.25, 0.3, 0.35, 0.4, 0.45, or 0.5%). In some embodiments the combinations, e.g., dry blended preparations, e.g., PGDBPs, do not comprise a slow onset sweetener, e.g., sucralose. In some embodiments, the combinations, e.g., dry blended preparations, e.g., PGDBPs, comprises a slow onset sweetener, e.g., sucralose, at a level less than 3.9% (w/w) (and optionally, at least 0.05, 0.1, 0.5, 1, or 2% (w/w)).

In some embodiments, the oral administration component comprises a coloring agent. Non-limiting examples of suitable color agents include food, drug and cosmetic colors (FD&C), drug and cosmetic colors (D&C), and external drug and cosmetic colors (Ext. D&C). The coloring agents can be used as dyes or their corresponding lakes.

In some embodiments, the oral administration component comprises a bitterness modifying agent. The bitterness modifying agent may reduce the bitterness or the perceived bitterness of the PGDBP. In some embodiments, the bitterness modifying agent is a bitterness covering agent, e.g., that increases a non-bitter flavor so that the taste perceived is less bitter. Bitterness covering agents include sweeteners. Examples of bitterness modifying agents, e.g., bitterness covering agents, include fenchone, borneol or isoborneol, menthol, and aspartame.

Particular oral administration components may include one or more of: citric acid, lecithin, (e.g. Alcolec F100), sweeteners (e.g. sucralose, sucralose micronized NF, Acesulfame potassium (e.g., Acelsulfame K or Ace-K)), a dispersion enhancer (e.g. xanthan gum (e.g. Ticaxan Rapid-3)), flavorings (e.g. vanilla custard #4306, Nat Orange WONF #1326, lime 865.0032U, and lemon 862.2169U), a bitterness masking agent (e.g. 936.2160U), and natural or artificial colorings (e.g. FD&C Yellow 6). In some embodiments, the oral administration component comprises lecithin. In other embodiments, the dry blended preparation, e.g., PGDBP, does not comprise lecithin.

flavor as a quality further comprises texture and/or mouth feel. Flavor is a composite characteristic that describes the sensations associated with a substance in a subject's mouth. In some embodiments, methods described herein further comprise evaluating a flavor of the dry blended preparation, e.g., PGDBP. In some embodiments, the general flavor of the dry blended preparation, e.g., PGDBP, is evaluated. In some embodiments, particular aspects of flavor are evaluated (e.g., bitterness, sweetness, sourness, saltiness, umami-ness, savoriness, metallic notes, or chemical burn). As used herein, taste as a quality comprises the sensations associated with a substance as experienced purely by the tongue/oral cavity, e.g., in the absence of olfactory/retronasal olfaction contribution. As used herein, aroma as a quality comprises the sensations associated with a substance as experienced via olfaction, e.g., including retronasal olfaction.

As used herein, texture as a quality comprises a property of a substance (e.g., combination, e.g., dry blended preparation, e.g., PGDBP, e.g., a formulation of a PGDBP described herein) that describes its granularity and consistency. For example, a substance may have a texture that is crumbly, tough, viscous, clumpy, etc. In some embodiments, texture is typically applied to solids, e.g., powders or foods. As used herein, mouthfeel as a quality comprises the touch sensations associated with a substance as experienced by the mouth.

In some embodiments, the dry blended preparation, e.g., PGDBP, is evaluated in dry form, e.g., as a powder. In some

TABLE 14

Exemplary Excipients for Orange Creamsicle Effect

| INGREDIENT | GRADE | FUNCTION | INCLUDE | RATIONALE |
|---|---|---|---|---|
| Citric Acid, Anhydrous | USP | pH, Flavor | No Change | f(volume) ≤ 1.0% w/v |
| Acesulfame Potassium (Ace-K) | NF | Sweetness (rapid onset) | Can be omitted | Target 1 Sweetener; Low HPLC Resolution |
| Sucralose, micronized | NF | Sweetness (slow onset) | No Change | Needed given no Ace-K, WHO ADI ≤ 15 mg/kg |
| Lecithin | FCC | Wetting Agent | Can be omitted | Potential API at higher doses; reduces HPLC column lifetime |
| Xanthan Gum, pre-hydrated | FCC | Stabilizer/Thickener | No Change | f(volume) ≤ 0.5% w/v; ≥0.1% w/v required (suspension) |
| Vanilla Custard Flavor (Artificial) | GRAS | Aroma | No Change | Masks sulfur; f(volume) ≤ 0.1% w/v |
| Orange Flavor (Natural and with other natural flavors (WONF)) | GRAS | 1° flavor | No Change | Citrus profile matches low pH; ≤1.0% w/v |
| Lime Flavor (Natural and WONF) | GRAS | 2° flavor | Can be omitted | 2° flavor profile not required; may use with or instead of orange; 1.0% w/v |
| Lemon Flavor (Natural Artificial) | GRAS | 2° flavor | Can be omitted | 2° flavor profile not required; may use with or instead of orange; ≤1.0% w/v |
| Taste Modifier | GRAS | Bitterness masker | Can be omitted | May be needed at low reconstitution volumes or if composition includes particularly bitter amino acid (e.g., tryptophan) |
| FD&C Yellow No. 6 | Certified | Provides orange color | No Change | Matches flavor profile |

Excipient Formulation Organoleptic Properties

In some embodiments, methods described herein further comprise evaluating an oral administration quality of the dry blended preparation, e.g., PGDBP. Oral administration qualities include but are not limited to flavor, taste, aroma, texture, mouth feel, and color. As used herein, flavor as a quality comprises taste and aroma. In some embodiments, embodiments, the dry blended preparation, e.g., PGDBP, is evaluated in liquid form, e.g., as an aqueous or oily suspension, emulsion, syrup, gel pack, or elixir. In some embodiments, the dry blended preparation, e.g., PGDBP, is evaluated in the form of a dietary composition, e.g., chosen from a medical food, a functional food, a supplement, or a nutriceutical.

Many methods of evaluating oral administration qualities are known to those skilled in the art and may be used to evaluate oral administration qualities in the methods described herein.

In some embodiments, evaluating an oral administration quality comprises evaluating the flavor, e.g., taste and/or aroma, of a dry blended preparation, e.g., PGDBP. In some embodiments, evaluating flavor comprises evaluating one, two, three, four, or all of the level of bitterness, sweetness, sourness, saltiness, umami-ness, savoriness, metallic notes, or chemical burn of a dry blended preparation, e.g., PGDBP. Bitterness can be evaluated by an animal preference test, human sensory evaluation (e.g., a group of human tasters evaluating a number of substances, e.g., scoring them relative to the PGDBP), by electronic tongue measurement, by in silico predictive methods (e.g., using software or searchable databases that, based on the structural/chemical features of the components of the PGDBP, predicts the bitterness of the PGDBP), or other methods known in the art.

In some embodiments, the taste of the combinations, e.g., dry blended preparations, e.g., PGDBPs, is less bitter than the taste of at least one amino acid entity of the combinations, e.g., dry blended preparations, e.g., PGDBPs, (e.g., an amino acid entity having a bitter taste). For example, the taste of a combination, e.g., dry blended preparation, e.g., PGDBP, comprising an arginine amino acid entity may be less bitter than the taste of the arginine amino acid entity, e.g., due to the presence of other components in the combination, e.g., dry blended preparation, e.g., PGDBP.

Excipients, e.g., oral administration components, can modify the oral administration qualities of the dry blended preparation, e.g., PGDBP. In some embodiments, the methods described herein further comprise, responsive to an evaluation of an oral administration quality, the addition or further addition of an excipient, e.g., oral administration component. In some embodiments, the excipient, e.g., oral administration component, added or further added masks or lessens the bitterness of the dry blended preparation, e.g., PGDBP.

Dosage Form

In some embodiments, the dry blended preparation, e.g., PGDBP, is formulated into a unit dosage of between about 4 g and about 80 g total amino acids (e.g., per day). In some embodiments, the dry blended preparation, e.g., PGDBP, is formulated into a unit dosage of about 5 g to about 15 g, about 10 g to about 20 g, about 20 g to about 40 g, or about 30 g to about 50 g total amino acids. In some embodiments, the dry blended preparation, e.g., PGDBP, is formulated into a unit dosage of about 5 g to about 15 g (e.g., about 6 g total amino acids. In an embodiment, the dry blended preparation, e.g., PGDBP, is formulated into a unit dosage comprising about 18 g total amino acids. In an embodiment, the dry blended preparation, e.g., PGDBP, is formulated into a unit dosage of about 23 g total amino acids. In an embodiment, the dry blended preparation, e.g., PGDBP, is formulated into a unit dosage of about 48 g total amino. In an embodiment, the dry blended preparation, e.g., PGDBP, is formulated into a unit dosage of about 68 g total amino acids is administered per day. In an embodiment, the dry blended preparation, e.g., PGDBP, is formulated into a unit dosage of about 72 g total amino acids. In some embodiments, the dry blended preparation, e.g., PGDBP, is formulated into a unit dosage of about 15 g to about 40 g (e.g., about 24 g total amino acids).

Downstream Processing

The methods of the present disclosure may comprise downstream processing steps, including dividing the PGDBP into portions (e.g., portioning) and fill-finish (e.g., formulation (e.g., with excipients), packaging, and labeling) and distribution. In some embodiments, a plurality of portions of a PGDBP that have been finalized by downstream processing steps meet a reference standard, e.g., the same reference standard(s) the PGDBP met. In the same embodiments, at least 50, 60, 70, 80, 85, 90, 95, 99, or 100% of the plurality of finalized portions meet the reference standard. In some embodiments, the PGDBP produced by a method described herein is sufficient such that a plurality of finalized portions meet a reference standard, e.g., the same reference standard(s) the PGDBP met. In the same embodiments, at least 50, 60, 70, 80, 85, 90, 95, 99, or 100% of the plurality of finalized portions meet the reference standard.

EXAMPLES

Example 1. Compositions

Two different oral compositions comprising bitter tasting amino acids have been prepared. Each composition is prepared as a dry powder for packaging in a stick pack. Multiple stickpacks can be combined for a single dose or daily dose, e.g., as exemplified below, 3, 6, or 9 stickpacks once, twice, or three times per day. To administer the preparation, the contents of the stick packs are dissolved or suspended in water. In both of the following examples, the aqueous suspension/solution had a pleasant orange creamsicle taste when informally tested by a panel of six individuals.

TABLE 15

| | | Active Moiety for Treatment of Cirrhosis | | |
|---|---|---|---|---|
| Ingredient | Grade | Stick Pack Dry Weight (g) | Stick Pack Dry Weight (% w/w/) | Low Daily Dose Weight (g)* | High Daily Dose Weight (g)** |
| L-Leucine | USP | 0.89 | 15.06 | 2.67 | 8.0 |
| L-Isoleucine | USP | 0.44 | 7.53 | 1.33 | 4.0 |
| L-Valine | USP | 0.89 | 15.06 | 2.67 | 8.0 |
| L-Lysine acetate | USP | 0.47 | 7.97 | 1.41 | 4.2 |
| L-Histidine | USP | 0.33 | 5.65 | 1.00 | 3.00 |
| L-Threonine | USP | 0.33 | 5.65 | 1.00 | 3.00 |
| L-Ornithine-L-Aspartate | >98% | 1.67 | 28.23 | 5.00 | 15.00 |
| Citric Acid, anhydrous | USP | 0.60 | 10.16 | 1.80 | 5.40 |
| Sucralose, micronized | NF | 0.016 | 0.27 | 0.048 | 0.144 |

TABLE 15-continued

Active Moiety for Treatment of Cirrhosis

| Ingredient | Grade | Stick Pack Dry Weight (g) | Stick Pack Dry Weight (% w/w/) | Low Daily Dose Weight (g)* | High Daily Dose Weight (g)** |
|---|---|---|---|---|---|
| Xanthan Gum, pre-hydrated | FCC | 0.08 | 1.36 | 0.24 | 0.72 |
| Vanilla Custard, artificial flavor | GRAS | 0.02 | 0.34 | 0.06 | 0.18 |
| Orange Flavor, natural WONF | GRAS | 0.16 | 2.71 | 0.48 | 1.44 |
| FD&C Yellow No. 6 | Certified | 0.0016 | 0.03 | 0.0048 | 0.0144 |
| Amino Acids (excluding acetate) | | 4.89 | 82.8 | 14.67 | 44.00 |
| Total | | 5.90 | 100.0 | 17.71 | 53.1307 |

*Low daily dose (14.7 g amino acids) based on 3 stick packs QD.
**High daily dose (44.0 g amino acids) based on 3 stick packs TID.

TABLE 16

Active Moiety for Treatment of Mild Traumatic Brain Injury

| Ingredient | Grade | Stick Pack Dry Weight (g) | Stick Pack Dry Weight (% w/w/) | Daily Dose Weight (g)* |
|---|---|---|---|---|
| L-Leucine | USP | 1.67 | 24.17 | 10.00 |
| L-Isoleucine | USP | 1.67 | 24.17 | 10.00 |
| L-Valine | USP | 1.67 | 24.17 | 10.00 |
| Acetylcysteine (NAC) | USP | 0.50 | 7.25 | 3.00 |
| Acetyl-L-Carnitine (ALCAR) HCl** | >98% | 0.24 | 3.42 | 1.42 |
| Citric Acid, anhydrous | USP | 0.60 | 8.70 | 3.60 |
| Sucralose, micronized | NF | 0.048 | 0.70 | 0.288 |
| Xanthan Gum, pre-hydrated | FCC | 0.24 | 3.48 | 1.44 |
| Vanilla Custard, artificial flavor | GRAS | 0.03 | 0.44 | 0.18 |
| Orange Flavor, natural WONF | GRAS | 0.24 | 3.48 | 1.44 |
| FD&C Yellow No. 6 | Certified | 0.0018 | 0.03 | 0.0108 |
| Amino Acids (excluding HCl) | | 5.70 | 82.7 | 34.20 |
| Total | | 6.896 | 100.0 | 41.37 |

*Daily dose (32.4 g amino acids excluding HCl salt) based on three stick packs BID.
**The daily dose of ALCAR independent of HCl is 1.2 g.

Example 2: Organoleptic Stability Testing

Experimental Summary

Organoleptic stability testing results showed that at ambient temperature the Placebo and all four amino acid blends remained similar to refrigerated controls and thus organoleptically acceptable for one year. Given the low degree of difference (DOD) scores from refrigerated controls at the end of the one year test period, the Placebo and all four amino acid blends would likely be acceptable for several more months. Therefore the Placebo and all four amino acid blends, from an organoleptic standpoint, when stored at ambient conditions can be used in clinical testing up to one year and possibly beyond from the date of manufacture.

Introduction

Amino acid formulations were designed to target and treat certain disease states. However, consuming amino acid supplemented beverages have challenges such as poor solubility and gritty texture, repugnant bitterness and aromas, unpleasant flavors and aftertaste, etc. In general, not only can these defects be present initially, but they also then tend to significantly increase over time, potentially creating unacceptable samples, unfit for human consumption. Therefore, a study was undertaken to monitor any organoleptic changes over time in prototype Placebo and four different amino acid composition-supplemented drink mixes.

Materials & Methods

As an overview, the organoleptic stability study protocol consisted of storing the samples, as single serve individual stick packs, at the following conditions:

Control Condition (refrigerated), 4° C.
Ambient Condition, 25° C., 60% RH
Accelerated Condition, 40° C., 75% RH The stick packs were pulled from storage chambers at various time points as described in the SOW and below. The powder contents of each stick pack was then reconstituted with water and evaluated by up to six panelists.

The following 5 samples were evaluated (see Table 17 attached hereto)

1. Placebo—Flavor, color and texture (Excipients) plus maltodextrin
2. Blend 1—Excipients plus FUSI-BCAA*, Arg, Glu, Acetyl-Cys
3. Blend 2—Excipients plus FUSI-BCAA*, Arg, Glu, Acetyl-Cys, Trp
4. Blend 3—Excipients plus FUSI-BCAA*, Arg, Glu, Acetyl-Cys, Leu
5. Blend 4—Excipients plus FUSI-BCAA*, Arg, Glu, Acetyl-Cys, Lys-Acetate, Thr, His, Phe
FUSI-BCAA: 2:1:1 instantized mixture of Leu, Ile, and Val, respectively Intensity Test Results & Discussion A summary of the results from the Intensity Test at T=0 and at T=1 month can be seen in Table 18, attached hereto. The intensity scores within each variable did not seem to significantly change from time 0 to month 1 as listed in Table 1; some scores increased, some decreased and some stayed the same but there was no clear pattern of change or deterioration of intensity. For example, for Blend 2 the Orange Aroma, Off-Aroma, Orange Flavor and Texture scored virtually the same, while the Color and Aftertaste increased and the Off-Flavor decreased form time 0 to 1 month. For each variable, Orange Flavor was tested using a statistical Two Sample Paired t-Test. The results from the t-Test showed that the Orange Flavor was not statistically significantly different (P=0.05, one tail) at time 0 versus 1 month. Calculations are shown in the Intensity Testing spreadsheet referenced above.

It was assumed that the powder product does not degrade or significantly change over time under the refrigerated control condition and therefore samples pulled from this chamber at each test date represent fresh or newly produced samples. As demonstrated in this intensity study, for 1 month, this hypothesis was validated, thereby achieving the current study's first objective to confirm the stability of the control condition.

DOD Test Results & Discussion

Accelerated Conditions:

In general, the attributes DOD scores were consistent with the Overall DOD score for each variable. The Overall DOD scores are listed in Table 19, attached. As shown in Table 19, in general and as expected, the Placebo and all four blends scored increasingly different from the control over time for the Overall DOD rating. The Overall DOD rating was the panelist's perception of the samples overall difference taking into account all the DOD attributes tested—color, aroma, flavor, mouthfeel and after taste. At the end of 3 months the Placebo, Blend 1 and 4 were rated as being having small to moderate differences from the control while Blends 2 and 3 were perceived as having moderate to large differences from the control. Based on our experience when samples scored 4 to 5 they were borderline acceptable and 5 and higher they were most likely unacceptable. Therefore, the Placebo and Blends 1 and 4 were acceptable after 3 months at accelerated conditions, while Blends 2 and 3 may be judged as unacceptable or close to being unacceptable.

It should be noted that 1 of 3 stick packs tested for Blend 2 had an average Overall DOD score of 6.4, while the other 2 stick packs scored around 3.8. The stick pack that scored 6.4 was described as having a "rotten egg smell", "putrid aroma", "awful flavor" and being "not palatable" and very "bitter". See below for discussion of why this one stick pack may have differed from the other two.

The process of chemical and biological reactions in food systems is dependent on many factors including but not limited to the amount of water available for reactions to occur, the temperature, the pH, the presence of enzymes or other catalysts. These reactions can be desired, as in the formation of characteristic flavors of aged cheese or undesirable as the case of sour milk or stale bread. The accelerated condition DOD test utilizes elevated temperature and humidity to increase these reactions as a way to predict what will happen at more normal, or ambient, storage conditions. A factor of 4× is generally consider the acceleration rate of these reactions.

If a 4× reaction increase factor is used, then the results from the accelerated condition test suggest that the Placebo and Blends 1 and 4 would only have small differences, while Blends 2 and 3 would have large differences from a control, or freshly made sample, after about 1 year (3 months times the 4× factor). The 4 blends contain a mixture of amino acids, which by their nature, are bioactive compounds susceptible to alteration or degradation by chemical and biological means. The Placebo on the other hand contains mostly maltodextrin which is relatively stable. Since the results show that Blends 1 and 4 aged similar to the Placebo then these formulation were relatively stable as well. Blend 2, which contained Tryptophan, as expected formed off flavors. Blend 3 was similar to Blend 1 in composition and only differed by added Leucine so it's not clear why this blend degraded. More research/information would be needed to determine a cause for this difference.

One piece of inconsistent data was, as mentioned above, one of the three Blend 2 samples had a significantly higher Overall DOD than the other 2 samples tested at the same time. Although more research/information would be needed to determine the exact cause, this extreme change could have been due to a leaky stick pack or poor stick pack seal. A leak or poor seal would allow moisture migration into the stick pack, which in turn would further accelerate the degradation reactions causing the extreme off aromas and flavors.

Ambient Conditions:

In general, the attributes DOD scores were consistent with the Overall DOD score within each variable. The Overall DOD scores can be seen below in Table 20, attached.

Conclusions/Next Steps

The Placebo and all four amino acid blends, from an organoleptic standpoint, did change over time, but only minimally and therefore can be used in clinical testing up to one year and likely beyond from the date of manufacture.

The invention claimed is:

1. A dry blended preparation comprising at least three amino acid entities and an excipient formulation, wherein the dry blended preparation is suitable for oral administration, wherein at least one amino acid entity has a bitter taste and the dry blended preparation has an acceptable taste, wherein the excipient formulation has fewer than eleven (11) ingredients, wherein the amino acid entities are not part of a peptide longer than 20 amino acids long, wherein the bitter tasting amino acid is arginine, valine, leucine, isoleucine, tryptophan, or phenylalanine; and one or both of:
   the excipient formulation comprises acesulfame, and acesulfame is present in the dry blended preparation at a level less than 1% (w/w); or
   the excipient formulation comprises sucralose, and sucralose is present in the dry blended preparation at a level less than 3.9% (w/w).

2. The dry blended preparation of claim 1, wherein the at least three amino acid entities comprise:
   (i) leucine, isoleucine, valine, lysine, histidine, threonine, and L-ornithine-L-aspartate;
   (ii) leucine, isoleucine, valine, acetylcysteine (NAC), and acetyl-L-carnitine (ALCAR);
   (iii) leucine, isoleucine, valine, arginine, histidine, and phenylalanine; or
   (iv) leucine, isoleucine, valine, and arginine.

3. The dry blended preparation of claim 1, which is: i) free of lecithin, ii) free of a bitterness masking agent, or iii) free of a rapid onset sweetener.

4. The dry blended preparation of claim 1, wherein the excipient formulation comprises Xanthan Gum.

5. The dry blended preparation of claim 1, wherein the excipient formulation comprises a pH modifying agent comprising citric acid.

6. The dry blended preparation of claim 1, wherein the excipient formulation comprises a single flavor agent comprising an orange citrus flavor.

7. The dry blended preparation of claim 1, wherein the excipient formulation comprises a vanilla custard aroma flavor agent.

8. The dry blended preparation of claim 1, wherein the excipient formulation comprises an orange coloring agent (colorant).

9. The dry blended preparation of claim 1, wherein the excipient formulation comprises a sweetener, a thickening agent, a pH modifying agent, a single flavor agent, an aroma flavor agent, and a coloring agent.

10. The dry blended preparation of claim 1, wherein the excipient consists of a sweetener, a thickening agent, a pH modifying agent, a single flavor agent, an aroma flavor agent, and a coloring agent.

11. The dry blended preparation of claim 9, wherein the sweetener is sucralose, wherein the thickening agent is Xanthan Gum, the pH modifying agent is citric acid, the flavor agent is an orange citrus flavor, the aroma flavor agent is vanilla custard, and the coloring agent is orange.

12. The dry blended preparation of claim 1, wherein the excipient formulation comprises sucralose, Xanthan Gum, citric acid for modifying pH, an orange citrus flavor agent, a vanilla custard aroma flavor agent, and an orange coloring agent.

13. The dry blended preparation of claim 1, wherein the excipient formulation consists of sucralose, Xanthan Gum, citric acid for modifying pH, an orange citrus flavor agent, a vanilla custard aroma flavor agent, and an orange coloring agent.

14. The dry blended preparation of claim 9, which is: i) free of lecithin, ii) free of a bitterness masking agent, or iii) free of a rapid onset sweetener.

15. The dry blended preparation of claim 1, wherein the excipient formulation is less than about 30% of the composition by weight.

16. The dry blended preparation of claim 1, which comprises at least four amino acid entities.

17. The dry blended preparation of claim 1, wherein the pH of the composition when dissolved in water is less than or equal to 6.

18. The dry blended preparation of claim 1, wherein the excipient formulation has fewer than ten (10), nine (9), eight (8), seven (7), six (6), or five (5) ingredients.

19. The dry blended preparation of claim 1, wherein the taste of the composition is less bitter than the taste of the at least one amino acid entity having a bitter taste.

20. The dry blended preparation of claim 1, wherein the dry blended preparation comprises less than or equal to 1% water by weight (w/w).

21. The dry blended preparation of claim 1, wherein the excipient formulation comprises acesulfame, and acesulfame is present in the composition at a level less than 1% (w/w).

22. The dry blended preparation of claim 1, wherein the excipient formulation comprises sucralose, and sucralose is present in the composition at a level less than 3.9% (w/w).

23. The dry blended preparation of claim 1, wherein:
the excipient formulation comprises acesulfame, and acesulfame is present in the composition at a level less than 1% (w/w); and
the excipient formulation comprises sucralose, and sucralose is present in the composition at a level less than 3.9% (w/w).

24. The dry blended preparation of claim 23, wherein the excipient formulation is less than about 20% of the dry blended composition by weight.

25. The dry blended preparation of claim 1, wherein the dry blended preparation is formulated into a unit dosage of between about 4 g and about 80 g total amino acids.

26. The dry blended preparation of claim 17, wherein the pH of the dry blended preparation when dissolved in water is from 3 to 4.6.

27. The dry blended preparation of claim 17, wherein the pH of the dry blended preparation when dissolved in water is from 3.5 to 6.

28. The dry blended preparation of claim 17, wherein the pH of the dry blended preparation when dissolved in water is from 3 to 5.

* * * * *